US010053514B2

(12) United States Patent
Bigner et al.

(10) Patent No.: US 10,053,514 B2
(45) Date of Patent: Aug. 21, 2018

(54) HUMAN BISPECIFIC EGFRVIII AND CD3 ANTIBODY ENGAGING MOLECULES

(71) Applicants: DUKE UNIVERSITY, Durham, NC (US); THE UNITED STATES OF AMERICA AS REPRESENTED BY THE SECRETARY OF HEALTH AND HUMAN SERVICES, NATIONAL INSTITUTES OF HEALTH, Washington, DC (US)

(72) Inventors: Darell D. Bigner, Mebane, NC (US); John Sampson, Durham, NC (US); Chien-Tsun Kuan, Cary, NC (US); Mingqing Cai, Durham, NC (US); Bryan D. Choi, Durham, NC (US); Patrick C. Gedeon, Durham, NC (US); Ira H. Pastan, Potomac, MD (US)

(73) Assignees: Duke University, Durham, NC (US); The United States of America as Represented by the Secretary of Health and Human Services, National Institutes of Health, Washington, DC (US)

( * ) Notice: Subject to any disclaimer, the term of this patent is extended or adjusted under 35 U.S.C. 154(b) by 3 days.

(21) Appl. No.: 14/903,659

(22) PCT Filed: Jul. 9, 2014

(86) PCT No.: PCT/US2014/046003
§ 371 (c)(1),
(2) Date: Jan. 8, 2016

(87) PCT Pub. No.: WO2015/006482
PCT Pub. Date: Jan. 15, 2015

(65) Prior Publication Data
US 2016/0168263 A1 Jun. 16, 2016

Related U.S. Application Data

(60) Provisional application No. 61/844,119, filed on Jul. 9, 2013.

(51) Int. Cl.
| | |
|---|---|
| *C07K 16/46* | (2006.01) |
| *A61K 39/395* | (2006.01) |
| *C12N 15/09* | (2006.01) |
| *C12N 15/11* | (2006.01) |
| *C07K 16/32* | (2006.01) |
| *C07K 16/28* | (2006.01) |
| *C07K 16/40* | (2006.01) |
| *A61K 39/00* | (2006.01) |

(52) U.S. Cl.
CPC .......... *C07K 16/32* (2013.01); *C07K 16/2809* (2013.01); *C07K 16/2863* (2013.01); *C07K 16/40* (2013.01); *A61K 2039/505* (2013.01); *C07K 2317/31* (2013.01); *C07K 2317/56* (2013.01); *C07K 2317/622* (2013.01); *C07K 2317/73* (2013.01)

(58) Field of Classification Search
None
See application file for complete search history.

(56) References Cited

U.S. PATENT DOCUMENTS

| | | | |
|---|---|---|---|
| 7,235,641 B2 | 6/2007 | Kufer et al. | |
| 7,575,923 B2 * | 8/2009 | Dorken | C07K 16/2809 |
| 7,728,114 B2 * | 6/2010 | Mach | C07K 16/2809 |
| 9,249,217 B2 * | 2/2016 | Bigner | C07K 16/2809 |
| 2010/0111979 A1 * | 5/2010 | Weber | A61K 47/48384 |
| 2012/0189630 A1 | 7/2012 | Bigner et al. | |
| 2015/0132306 A1 | 5/2015 | Bigner et al. | |

FOREIGN PATENT DOCUMENTS

| | | |
|---|---|---|
| WO | 2005010151 A2 | 2/2005 |
| WO | 2005118635 A2 | 12/2005 |
| WO | WO 2008119567 A2 * | 10/2008 ........... C07K 16/082 |
| WO | 2013185010 A1 | 12/2013 |

OTHER PUBLICATIONS

Reiter et al., Engineering antibody Fv fragments for cancer detection and therapy: Disulfide-stabilized Fv fragments, Nature Biotech. 14:1239-1245, Oct. 1996.*
Holliger, Engineered antibody fragments and the rise of single domains, Nature Biotech. 23(9):1126-1136, Sep. 2005.*
Lutterbuese et al., Potent contro of tumor growth by CEA/CD3-bispecific single-chain antibody constructs that are not competitively inhibited by soluble CEA, J. Immunol.32(4):341-352, 2009.*
Batra et al., Anti-Tac(Fv)-PE40, a single chain antibody Pseudomonas fusion protein directed at interleukin 2 recptor bearing cells, J. Biol. Chem. 265(25):15198-15202, 1990.*
Whitlow et al., An improved linker for single-chain Fv with reduced aggregation and enhanced proteolytic stability, Prot. Eng. 6(8): 989-995, 1993.*
Stamova et al., Cancer immunotherapy by retargeting the immune effector cells via recombinant bispecific antibody constructs, Antibodies, 1:172-198, Jul. 18, 2012 (Year: 2012).*
Japan Agency for Med. Res. Dev., Research and development projects adopted in FY2015: Development of manufacturing technology on small bispecifc antibody for next generation biologics. Retrieved Feb. 6, 2018 [online]. Retrieved from the internet <URL:http://www.i-biomed.jp/en/subject/2015/01/>. (Year: 2015).*
Extended European Search Report issued in corresponding European Application No. 14823231.7, dated Feb. 14, 2017.
Choi et al. "Systemic administration of a bispecific antibody targeting EGFRvIII successfully treats intracerebral glioma," PNAS, vol. 110, No. 1, Dec. 17, 2012, pp. 270-275.

(Continued)

*Primary Examiner* — Claire Kaufman
(74) *Attorney, Agent, or Firm* — Banner & Witcoff, Ltd.

(57) ABSTRACT

We have constructed a polynucleotide encoding a bispecific antibody engaging molecule which has one arm that specifically engages a tumor cell which expresses the human EGFRvIII mutant protein on its surface, and a second arm that specifically engages T cell activation ligand CD3. The polynucleotide is codon optimized for expression in CHO cells. The subunits of the engaging molecules are organized to achieve greater efficiency. These are therapeutic agents.

8 Claims, No Drawings

(56) References Cited

OTHER PUBLICATIONS

Zitron et al., "Targeting and killing of glioblastoma with activated T cells armed with bispecific antibodies," BMC Cancer, vol. 13, No. 1, Feb. 22, 2013, p. 83.
Choi et al., "Rational design and generation of recombinant control reagents for bispecific antibodies through CDR mutagenesis," Journal of Immunological Methods, vol. 395, No. 1, Jun. 24, 2013, pp. 14-20.
Ohno et al., "Retrovirally engineered T-cell-based immunotherapy targeting type III variant epidermal growth factor receptor, a glioma-associated antigen," Cancer Science, vol. 101, No. 12, Dec. 30, 2010, pp. 2518-2524.
Shen et al., "Chimeric antigen receptor containing ICOS signaling domain mediates specific and efficient antitumor affect of T cells against EGFRvIII expressing glioma," Journal of Hematology & Oncology, vol. 6, No. 1, May 9, 2013, p. 33.
Japanese Office Action dated Dec. 5, 2016 in related JP Application No. 2016-525458.
NCBI GenBank accession No. U26274.1 (May 17, 1996).
Choi et al., 'A novel bispecific antibody recruits T cells to eradicate tumors in the "immunologically privileged" central nervous system' Oncoimmunology, vol. 2, No. 4, pp. e23639-1-e23639-2 (Apr. 2013).
Choi, et al., 'Bispecific antibodies engage T cells for antitumor immunotherapy' Expert Opinion on Biological Therapy, vol. 11, No. 7, pp. 843-853 (2011).
International Search Report—PCT/US2014/046003—dated Oct. 27, 2014.

\* cited by examiner

HUMAN BISPECIFIC EGFRVIII AND CD3 ANTIBODY ENGAGING MOLECULES

This invention was made using funds from the U.S. government. The U.S. government retains certain rights in the invention according to the terms of NIH/NCI grant no. CA11898.

TECHNICAL FIELD OF THE INVENTION

This invention is related to the area of cancer therapy. In particular, it relates to treating cancers that express EGFRvIII and agents for doing the same.

BACKGROUND OF THE INVENTION

The most common primary malignant brain tumor, glioblastoma multiforme (GBM), remains uniformly fatal despite surgical resection, radiation therapy, and chemotherapy1. Immunotherapy promises to induce robust, tumor-specific immune responses that eliminate neoplastic cells with unparalleled specificity without adding additional toxicity to multimodality therapy. Substantial evidence supports the role of T-cells in the eradication of cancer. Recently, the concept of using specific antibodies to re-direct T-cells has been optimized in the form of recombinant bispecific T-cell engaging molecules, or bispecific T-cell engaging molecules, that consist of a tumor-targeting single-chain antibody connected to a single-chain antibody directed against a Tcell activation ligand such as CD3. These bispecific T cell engaging molecules can tether T-cells to tumor cells, which results in a highly localized and specific activation of T-cells with concomitant tumor cell lysis. Recently, human trials using a CD19×CD3 bispecific T cell engaging molecule confirmed the potency of these constructs by tumor regression observed in 7/7 patients with non-Hodgkin's lymphoma at a dose of only 0.06 mg/m2 with clearance of tumor from the blood, bone marrow, and liver4. The most significant limitation of these promising constructs, however, is the lack of tumor-specific targets that are frequently and homogeneously expressed.

Tumor-specific antigens derived from mutations in somatic genes are less likely to be associated with autoimmunity, but often arise randomly as a result of the genetic instability of tumors and, as such, tend to be patient-specific and incidental to the oncogenic process. EGFRvIII, however, is a frequent and consistent tumor specific mutation, central to the neoplastic process, which consists of an in-frame deletion of 801 base pairs from the extracellular domain (ECD) of the EGFR that splits a codon and produces a novel glycine at the fusion junction. This mutation encodes a constitutively active tyrosine kinase that enhances neoplastic cell growth and migration9 and confers radiation and chemotherapeutic resistance to tumor cells. The EGFRvIII mutation is most frequently seen in patients with GBM, but has been found in a broad array of other common cancers. The new glycine inserted at the fusion junction of normally distant parts of the ECD results in a tumor-specific epitope that is not found in any normal tissues.

There is a continuing need in the art to find better and more successful treatments of cancers such as brain cancers.

SUMMARY OF THE INVENTION

One aspect of the invention is a bispecific polypeptide. The bispecific polypeptide comprises a first human single chain variable region which binds to EGFRvIII. The first single chain variable region is in series in amino to carboxy order with a second human single chain variable region. The second single chain variable region binds to T cell activation ligand CD3. The first single chain variable region comprises segments encoded by SEQ ID NO: 5 and 6 in amino to carboxy order. The second single chain variable region comprises segments encoded by SEQ ID NO: 7 and 8 in amino to carboxy order.

Another aspect of the invention is a polynucleotide encoding the bispecific polypeptide. The bispecific polypeptide comprises a first human single chain variable region which binds to EGFRvIII. The first single chain variable region is in series in amino to carboxy order with a second human single chain variable region. The second single chain variable region binds to T cell activation ligand CD3. The first single chain variable region comprises segments encoded by SEQ ID NO: 5 and 6 in amino to carboxy order. The second single chain variable region comprises segments encoded by SEQ ID NO: 7 and 8 in amino to carboxy order. A particular polynucleotide encoding the bispecific polypeptide is shown in SEQ ID NO: 1.

Another aspect of the invention is a method of treating an EGFRvIII-expressing tumor in a patient. The bispecific polypeptide is administered to the patient, whereby a cytolytic T cell response to the tumor is induced. The bispecific polypeptide comprises a first human single chain variable region which binds to EGFRvIII. The first single chain variable region is in series in amino to carboxy order with a second human single chain variable region. The second single chain variable region binds to T cell activation ligand CD3. The first single chain variable region comprises segments encoded by SEQ ID NO: 5 and 6 in amino to carboxy order. The second single chain variable region comprises segments encoded by SEQ ID NO: 7 and 8 in amino to carboxy order.

Still another aspect of the invention is a method of making the bispecific polypeptide. A cell is cultured in a culture medium. The cell comprises a polynucleotide encoding the bispecific polypeptide. The bispecific polypeptide comprises a first human single chain variable region which binds to EGFRvIII. The first single chain variable region is in series in amino to carboxy order with a second human single chain variable region. The second single chain variable region binds to T cell activation ligand CD3. The first single chain variable region comprises segments encoded by SEQ ID NO: 5 and 6 in amino to carboxy order. The second single chain variable region comprises segments encoded by SEQ ID NO: 7 and 8 in amino to carboxy order. After culturing, the bispecific polypeptide is harvested from the cells or from the culture medium.

These and other embodiments which will be apparent to those of skill in the art upon reading the specification provide the art with

DETAILED DESCRIPTION OF THE INVENTION

The inventors have developed human bispecific T cell engaging molecules which target both the EGFRvIII and T cell activation ligand CD3. They have been found to recruit cytotoxic T cells to a cancer cell expressing EGFRvIII and activate cytotoxic T cells, thereby killing the cancer cell expressing the EGFRvIII molecule. The bispecific T cell engaging molecules are selectively reactive with EGFRvIII and T cell activation ligand CD3 displayed on the surface of mammalian cells which are accessible to the antibody from the extracellular milieu. Of particular note are human bispecific T cell engaging molecules in which the $V_L$ segment precedes the $V_H$ segment of the variable region which binds to EGFRvIII. Of additional note are fusion proteins that contain a signal peptide. Moreover, polynucleotides that encode the human bispecific T cell engaging molecules may be codon optimized for expression in Chinese Hamster Ovary (CHO) cells.

Fusion proteins that are human bispecific T cell engaging molecules may or may not contain linker molecules between individual variable domains and between variable regions. The linker may be selected from those shown in SEQ ID NO: 9 and 10, or those which have a different number of monomers as shown in SEQ ID NO: 10, ranging from 1-5, 5-10 or 1-10. Other linkers as are known in the art may be used as well.

A signal sequence can be used at the amino terminal end of the fusion protein to facilitate secretion of the human bispecific T cell engaging molecules from the producing cells in culture. Secretion is advantageous as it avoids the need to break cells to harvest the fusion protein product from the cells. While the signal sequence shown in SEQ ID NO: 4 has been shown to successfully guide secretion of the human bispecific T cell engaging molecules, other signal sequences known in the art may be used as alternatives.

Although the nucleic acid encoding the human bispecific T cell engaging molecules shown in SEQ ID NO: 1 has been codon optimized for CHO cells, the same human bispecific T cell engaging molecules can be made from other nucleic acids which encode the same amino acids but use different codons. These may be optimized for production in different cell lines or in different animal systems in vivo.

Although the order of the variable domains presented in SEQ ID NO: 1, 2, and 3 appears to be highly efficient, other orders of the variable domains may be used to achieve other human bispecific T cell engaging molecules, which may share certain properties but have other beneficial properties that are unique. For example, production may be optimized with one order of domains, whereas avidity or cytotoxicity may be optimized with another order. Possible orders of the variable domains include: SEQ ID NO: 5, 6, 7, 8; SEQ ID NO: 8, 7, 6, 5; SEQ ID NO: 6, 5, 7, 8; SEQ ID NO: 5, 6, 8, 7; SEQ ID NO: 8, 7, 5, 6; and SEQ ID NO: 6, 5, 8, 7. Linkers may be used between any of these segments. Signal sequences may precede N-terminally any of these sequences of domains.

Many types of bispecific antibodies can be constructed and used. These include, without limitation, quadroma-derived F(ab')2, heterodimeric scFv, heterodimeric Fab, diabodies, tandem diabodies, and tandem scFv molecules. Bispecific antibodies can also be made using trifunctional antibodies, i.e., antibodies that have a third specificity as well as the initial two for EGFRvIII and a T cell activation ligand. The many forms are well known in the art.

Once bispecific T cell engaging molecules have been constructed, they can be produced in recombinant cells. Any suitable cell type can be used. If the bispecific T cell engaging molecules are secreted, they can be harvested from the culture medium. If they remain intracellular, the cells can be collected and broken under suitable conditions to harvest the bispecific T cell engaging molecules from the appropriate cell fraction. Any convenient cell host can be used for producing the bispecific T cell engaging molecules, including bacteria, yeast, insect cells, plant cells, algal cells, mammalian cells. In one scenario, the bispecific T cell engaging molecules can be produced in stably transfected CHO cells and the supernatant will contain the produced bispecific T cell engaging molecules.

Any tumor which expresses EGFRvIII can be targeted and treated with the bispecific T cell engaging molecules. Tumors which have been found to express the EGFRvIII antigen include brain tumors such as glioblastoma multiforme, breast tumors, and lung tumors. Any of these or other tumors can be targeted if it expresses the mutant antigen.

Definitions

Units, prefixes, and symbols are denoted in their Systeme International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the disclosure which can be had by reference to the specification as a whole. Accordingly, the terms defined immediately below are more fully defined by reference to the specification in its entirety.

"EGFRvIII" means a mutant form of the epidermal growth factor receptor recognized by MR1 scFv and characterized by an 801 base pair in frame deletion of exons 2 to 7 near the amino terminal. This form of the receptor is known in the art, as exemplified by the Wickstrand et al., Moscatello et al., and Lorimer et al. references cited in the Background. Due to a change in terminology, EGFRvIII was originally termed a Type II mutation in some earlier work in the field, as exemplified by U.S. Pat. No. 5,212,290.

The term "CD3" refers to the protein complex associated with the T cell receptor. Antibodies directed against CD3 are able to generate an activation signal in T lymphocytes. Other T cell activation ligands can be used as well, including without limitation CD28, CD134, CD137, and CD27.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies), heteroconjugate antibodies (e.g., bispecific antibodies) and recombinant single chain Fv fragments (scFv), disulfide stabilized (dsFv) Fv fragments (See, U.S. Ser. No. 08/077,252, incorporated herein by reference), or pFv fragments (See, U.S. Provisional Patent Applications 60/042,350 and 60/048,848, both of which are incorporated herein by reference.). The term "antibody" also includes antigen binding forms of antibodies (e.g., Fab', F(ab')2, Fab, Fv and rIgG (See also, Pierce Catalog and Handbook, 1994-1995 (Pierce Chemical Co., Rockford, Ill.).

An antibody immunologically reactive with a particular antigen can be generated by recombinant methods such as selection of libraries of recombinant antibodies in phage or similar vectors (See, e.g., Huse, et al., Science 246:1275-1281 (1989); Ward, et al., Nature 341:544-546 (1989); and Vaughan, et al., Nature Biotech. 14:309-314 (1996)).

Typically, an immunoglobulin has a heavy and light chain. Each heavy and light chain contains a constant region and a variable region. Light and heavy chain variable regions contain a "framework" region interrupted by three hypervariable regions, also called complementarity-determining regions or CDRs. The extent of the framework region and CDRs have been defined (see, SEQUENCES OF PROTEINS OF IMMUNOLOGICAL INTEREST, Kabat, E., et al., U.S. Department of Health and Human Services, (1987); which is incorporated herein by reference). The sequences of the framework regions of different light or heavy chains are relatively conserved within a species. The framework region of an antibody, that is the combined framework regions of the constituent light and heavy chains, serves to position and align the CDRs in three dimensional space. The CDRs are primarily responsible for binding to an epitope of an antigen. The CDRs are typically referred to as CDR1, CDR2, and CDR3, numbered sequentially starting from the N-terminus.

The phrase "single chain Fv" or "scFv" refers to an antibody in which the heavy chain and the light chain of a traditional two chain antibody have been joined to form one chain. Typically, a linker peptide is inserted between the two chains to allow for proper folding and creation of an active binding site.

The term "linker peptide" includes reference to a peptide within an antibody binding fragment (e.g., Fv fragment) which serves to indirectly bond the variable heavy chain to the variable light chain. The linker may be a series of a single amino acid or an alternating pattern of amino acids, for example.

The term "contacting" includes reference to placement in direct physical association. With regards to this invention, the term refers to antibody-antigen binding.

As used herein, the term "bispecific T-cell engaging molecule" refers to a molecule designed to harness a subject's T cells to kill cancer cells by targeting to the tumor cells expressing a desired molecule. In certain embodiments, the desired molecule is human EGFRvIII. In other embodiments, the bispecific T cell engaging molecules comprises two Fv domains. In other embodiments, the bispecific T cell engaging molecule comprises a first Fv domain directed to EGFRvIII and a second Fv domain directed to CD3. The Fv domains may be scFv domains.

The term "selectively reactive" includes reference to the preferential association of an antibody, in whole or part, with a cell or tissue bearing EGFRvIII or CD3 and not to cells or tissues lacking EGFRvIII or CD3. It is, of course, recognized that a certain degree of non-specific interaction may occur between a molecule and a non-target cell or tissue. Nevertheless, selective reactivity, may be distinguished as mediated through specific recognition of EGFRvIII and CD3. Although selectively reactive antibodies bind antigen, they may do so with low affinity. On the other hand, specific binding results in a much stronger association between the antibody and cells bearing EGFRvIII or CD3 than between the bound antibody and cells lacking EGFRvIII or CD3 or low affinity antibody-antigen binding. Specific binding typically results in greater than 2-fold, preferably greater than 5-fold, more preferably greater than 10-fold and most preferably greater than 100-fold increase in amount of bound antibody (per unit time) to a cell or tissue bearing EGFRvIII or CD3 as compared to a cell or tissue lacking EGFRvIII or CD3. Specific binding to a protein under such conditions requires an antibody that is selected for its specificity for a particular protein. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, ANTIBODIES, A LABORATORY MANUAL, Cold Spring Harbor Publications, New York (1988), for a description of immunoassay formats and conditions that can be used to determine specific immunoreactivity. In some embodiments of the invention the antibody will bind to EGFRvIII better than to wild-type EGFR. In some instances an antibody will bind to both. The differential binding may be reflected in a stronger binding, or in a faster binding, or in more binding to a fixed amount of antigen with a fixed amount of time. The better binding may be by a factor of at least 2, 4, 6, 8, or 10. Under some disease conditions, it may be advantageous to have some degree of binding to both mutant and wild-type forms of EGFR, for example where both forms are co-expressed on a tumor target. Under other disease situations, it may be desirable to have the maximum amount of specify available for the mutant form, for example, to reduce adverse side effects.

As used herein, "polypeptide," "peptide," and "protein" are used interchangeably and include reference to a polymer of amino acid residues. The terms apply to amino acid polymers in which one or more amino acid residue is an artificial chemical analogue of a corresponding naturally occurring amino acid, as well as to naturally occurring amino acid polymers. The terms also apply to polymers containing conservative amino acid substitutions such that the protein remains functional.

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

The phrase "disulfide bond" or "cysteine-cysteine disulfide bond" refers to a covalent interaction between two cysteines in which the sulfur atoms of the cysteines are oxidized to form a disulfide bond. The average bond energy of a disulfide bond is about 60 kcal/mol compared to 1-2 kcal/mol for a hydrogen bond. In the context of this invention, the cysteines which form the disulfide bond are within the framework regions of the single chain antibody and serve to stabilize the conformation of the antibody. Cysteine residues can be introduced, e.g., by site directed mutagenesis, so that stabilizing disulfide bonds can be made within the molecule.

As used herein, "recombinant" includes reference to a protein produced using cells that do not have, in their native state, an endogenous copy of the DNA able to express the protein. The cells produce the recombinant protein because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, under expressed or not expressed at all.

As used herein, "nucleic acid" or "nucleic acid sequence" includes reference to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof as well as conservative variants, i.e., nucleic acids present in wobble positions of codons and variants that, when translated into a protein, result in a conservative substitution of an amino acid.

As used herein, "encoding" with respect to a specified nucleic acid, includes reference to nucleic acids which comprise the information for translation into the specified protein. The information is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (*Proc. Nat'l Acad. Sci. USA* 82:2306-2309 (1985), or the ciliate Macronucleus, may be used when the nucleic acid is expressed in using the translational machinery of these organisms. Any codon for an amino acid may be substituted for another codon for the same amino acid without changing the encoded protein. Translation efficiency may, however, be modified.

The phrase "fusing in frame" refers to joining two or more nucleic acid sequences which encode polypeptides so that the joined nucleic acid sequence translates into a single chain protein which comprises the original polypeptide chains.

As used herein, "expressed" includes reference to translation of a nucleic acid into a protein. Proteins may be expressed and remain intracellular, become a component of the cell surface membrane or be secreted into the extracellular matrix or medium.

By "host cell" is meant a cell which can support the replication or expression of the expression vector. Host cells may be prokaryotic cells such as *E. coli*, or eukaryotic cells such as yeast, insect, amphibian, or mammalian cells.

The phrase "phage display library" refers to a population of bacteriophage, each of which contains a foreign cDNA recombinantly fused in frame to a surface protein. The phage displays the foreign protein encoded by the cDNA on its surface. After replication in a bacterial host, typically *E. coli*, the phage which contain the foreign cDNA of interest are selected by the expression of the foreign protein on the phage surface.

"Sequence identity" in the context of two nucleic acid or polypeptide sequences includes reference to the nucleotides (or residues) in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers & Miller, Computer Applic. Biol. Sci. 4:11-17 (1988), e.g., as implemented in the program PC/GENE (Intelligenetics, Mountain View, Calif., USA). An indication that two peptide sequences are substantially similar is that one peptide is immunologically reactive with antibodies raised against the second peptide. Thus, a peptide is substantially similar to a second peptide, for example, where the two peptides differ only by a conservative substitution.

A "comparison window," as used herein, includes reference to a segment of about 10-20 residues in which a sequence may be compared to a reference sequence of the same number of contiguous positions after the two sequences are optimally aligned. Methods of alignment of sequences for comparison are well known in the art. Optimal alignment of sequences for comparison may be conducted by the local homology algorithm of Smith & Waterman, Adv. Appl. Math. 2:482 (1981); by the homology alignment algorithm of Needleman & Wunsch, J. Mol. Biol. 48:443 (1970); by the search for similarity method of Pearson & Lipman, Proc. Nat'l Acad. Sci. USA 85:2444 (1988); by computerized implementations of these algorithms (including, but not limited to CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), Madison, Wis., USA); the CLUSTAL program is well described by Higgins & Sharp, Gene 73:237-244 (1988) and Higgins & Sharp, CABIOS 5:151-153 (1989); Corpet, et al., Nucl. Acids Res. 16:10881-90 (1988); Huang, et al., Computer Applications in the Biosciences 8:155-65 (1992); and Pearson, et al., Meth. in Molec. Biol. 24:307-31 (1994).

The terms "effective amount" or "amount effective to" or "therapeutically effective amount" include reference to a dosage of a therapeutic agent sufficient to produce a desired result, such as inhibiting cell protein synthesis by at least 50%, or killing the cell.

The term "therapeutic agent" includes any number of compounds currently known or later developed to act as anti-neoplastics, anti-inflammatories, cytokines, anti-infectives, enzyme activators or inhibitors, allosteric modifiers, antibiotics or other agents administered to induce a desired therapeutic effect in a patient.

The term "in vivo" includes reference to inside the body of the organism from which the cell was obtained. "Ex vivo" and "in vitro" means outside the body of the organism from which the cell was obtained.

Once the nucleic acids encoding a bispecific T cell engaging molecule of the present disclosure are isolated and cloned, one may express the desired protein in a recombinantly engineered cell such as bacteria, plant, yeast, insect, and mammalian cells. It is expected that those of skill in the art are knowledgeable in the numerous expression systems available for expression of proteins including *E. coli*, other bacterial hosts, yeast, and various higher eukaryotic cells such as the COS, CHO, HeLa and myeloma cell lines. No attempt to describe in detail the various methods known for the expression of proteins in prokaryotes or eukaryotes will be made. In brief, the expression of natural or synthetic nucleic acids encoding the isolated proteins of the invention will typically be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain transcription and translation terminators, initiation sequences, and promoters useful for regulation of the expression of the DNA encoding the protein. To obtain high level expression of a cloned gene, it is desirable to construct expression cassettes which contain, at the minimum, a strong promoter to direct transcription, a ribosome binding site for translational initiation, and a transcription/translation terminator. For *E. coli* this includes a promoter such as the T7, trp, lac, or lambda promoters, a ribosome binding site and preferably a transcription termination signal. For eukaryotic cells, the control sequences can include a promoter and preferably an enhancer derived from immunoglobulin genes, SV40, cytomegalovirus, and a polyadenylation sequence, and may include splice donor and acceptor sequences. The cassettes of the invention can be transferred into the chosen host cell by well-known methods such as calcium chloride transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes. It is also contemplated that the DNA can be delivered to a recipient patient, for example, on nanoparticles or other DNA delivery system, and that the patient may produce her own bispecific T-cell engaging molecules in vivo.

One of skill would recognize that modifications can be made to a nucleic acid encoding a polypeptide of the present disclosure (i.e., anti-EGFRvIII or anti-CD3) without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

The phrase "malignant cell" or "malignancy" refers to tumors or tumor cells that are invasive and/or able to undergo metastasis, i.e., a cancerous cell.

In addition to recombinant methods, the bispecific T cell engaging molecules of the present disclosure can also be constructed in whole or in part using standard peptide synthesis. Solid phase synthesis of the polypeptides of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, THE PEPTIDES: ANALYSIS, SYNTHESIS, BIOLOGY. VOL. 2: SPECIAL METHODS IN PEPTIDE SYNTHESIS, PART A. pp. 3-284; Merrifield, et al. J. Am. Chem. Soc. 85:2149-2156 (1963), and Stewart, et al., SOLID PHASE PEPTIDE SYNTHESIS, 2ND ED., Pierce Chem. Co., Rockford, Ill. (1984). Proteins of greater length may be synthesized by condensation of the amino and carboxyl termini of shorter fragments. Methods of forming peptide bonds by activation of a carboxyl terminal end (e.g., by the use of the coupling reagent N,N'-dicycylohexylcarbodiimide) are known to those of skill.

In addition to redirecting T-cells to tumor-specific antigens, the bispecific T cell engaging molecules can also be used to carry other diagnostic or therapeutic compounds to cells expressing EGFRvIII on their surface. Thus, a bispecific T cell engaging molecule may be attached directly or indirectly, e.g., via a linker, to a drug so that it will be delivered directly to cells bearing EGFRvIII. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to the bispecific T cell engaging molecule may be an encapsulation system, such as a liposome or micelle that contains a therapeutic composition such as a drug, a nucleic acid (e.g. an antisense nucleic acid), or another therapeutic moiety that is preferably shielded from direct exposure to the circulatory system. Means of preparing liposomes attached to antibodies are well known to those of skill in the art. See, for example, U.S. Pat. No. 4,957,735; and Connor, et al., Pharm. Ther. 28:341-365 (1985).

The bispecific T cell engaging molecules of this disclosure are particularly useful for parenteral administration, such as intravenous administration or administration into a body cavity or lumen of an organ. For example, ovarian malignancies may be treated by intravenous administration or by localized delivery to the tissue surrounding the tumor. For treatment of tumors in the brain, the molecules may be delivered directly to the brain, for example by injection or the molecules can be administered intravenously and then cross the blood brain barrier.

The compositions for administration will commonly comprise a solution of the bispecific T cell engaging molecules dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical pharmaceutical composition of the present invention for intravenous administration would be about 0.1 to 10 mg per patient per day. Dosages from 0.1 up to about 100 mg per patient per day may be used, particularly if the drug is administered to a secluded site and not into the circulatory or lymph system, such as into a body cavity or into a lumen of an organ. Actual methods for preparing administrable compositions will be known or apparent to those skilled in the art and are described in more detail in such publications as REMINGTON'S PHARMACEUTICAL SCIENCE, 19TH ED., Mack Publishing Company, Easton, Pa. (1995).

The compositions of the present invention can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health. An effective amount of the compound is that which provides either subjective relief of a symptom(s) or an objectively identifiable improvement as noted by the clinician or other qualified observer.

Single or multiple administrations of the compositions are administered depending on the dosage and frequency as required and tolerated by the patient. In any event, the composition should provide a sufficient quantity of the proteins of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

Controlled release parenteral formulations of the pharmaceutical compositions of the present disclosure can be made as implants, oily injections, or as particulate systems. For a broad overview of protein delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, e.g., Kreuter, J., COLLOIDAL DRUG DELIVERY SYSTEMS, J. Kreuter, ed., Marcel Dekker, Inc., New York, N.Y., pp. 219-342 (1994); and Tice & Tabibi, TREATISE ON CONTROLLED DRUG DELIVERY, A. Kydonieus, ed., Marcel Dekker, Inc. New York, N.Y., pp. 315-339 (1992) both of which are incorporated herein by reference.

Polymers can be used for ion-controlled release of pharmaceutical compositions of the present invention. Various degradable and nondegradable polymeric matrices for use in controlled drug delivery are known in the art (Langer, R., Accounts Chem. Res. 26:537-542 (1993)). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston, et al., Pharm. Res. 9:425-434 (1992); and Pec, et al., J. Parent. Sci. Tech. 44(2):58-65 (1990)). Alternatively, hydroxyapatite has been used as a microcarrier for controlled release of proteins (Ijntema, et al., Int. J. Pharm. 112:215-224 (1994)). In yet another aspect, liposomes are used for controlled release as well as drug targeting of the lipid-capsulated drug (Betageri, et at., LIPOSOME DRUG DELIVERY SYSTEMS, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

Among various uses of the bispecific T cell engaging molecules of the present invention are included a variety of disease conditions caused by specific human cells that may be eliminated by the toxic action of the fusion protein. One preferred application for the bispecific T cell engaging molecules of the invention is the treatment of malignant cells expressing EGFRvIII. Exemplary malignant cells include astrocytomas, glioblastomas, melanoma and the like.

As used herein, "mammalian cells" includes reference to cells derived from mammals including humans, rats, mice, guinea pigs, chimpanzees, or macaques. The cells may be cultured in vivo or in vitro.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLES

Example 1

We constructed the molecule MR1-1XaCD3, which consists of MR1-1, the murine anti-human EGFRvIII single-chain Fv, and aCD3, the murine anti-human CD3 single-chain Fv. MR1-1XaCD3 was expressed in and purified from bacteria BL21 (DE3), and the activity of this double function molecule was confirmed by FACS showing its specific binding to EGFRvIII-expressing cell lines, as well as human T cells. The cytotoxicity of MR1-1XaCD3 on EGFRvIII-expressing GBM D54MG.EGFRvIII cell lines was measured in vitro by standard chromium release assay. The efficacy of MR1-1XaCD3 was evaluated in NOD/SCID gamma mice where human EGFRvIII-expressing cell lines were implanted. Our results showed that the MR1-1xaCD3 construct is highly cytotoxic and antigen-specific, with an 8-fold increase in specific lysis for D54MG.EGFRvIII over the wild-type control. In a subcutaneous model, tumor growth was inhibited at a dose dependent manner. While total inhibition was achieved at the 100 mcg/mouse/day, low dose might work effectively upon optimization. In summary, our experiments showed that a human EGFRvIII-specific T-cell engaging molecules, MR1-1XaCD3, is effective on EGFRvIII-expressing tumor.

A murine MAb scFv MR1-1, specific for EGFRvIII, has been demonstrated to be a suitable vehicle for GBM treatment in the format of recombinant immunotoxins, which is now in a clinical trial at our institution (BB-IND-12,589). However, the innate properties of murine-derived antibodies might induce neutralizing antibodies that limit their wider application. Therefore, fully human MAbs are more desirable for the construction of recombinant bispecific T cell engaging molecules for clinical trials.

To obtain high-affinity human anti-EGFRvIII MAbs and scFvs we will (1) fuse EGFRvIII-specific B-cells to the HMMA2.5 non-secreting myeloma partner using an electrofusion technique or (2) clone the variable heavy and light chains from DNA libraries prepared from the antibody-secreting B-cell clones derived directly from GBM patients who have been vaccinated with an EGFRvIII-specific epitope.

In the context of an ongoing clinical trial in these patients, we have shown that vaccination with an EGFRvIII-specific peptide (PEPvIII) induced high-titer antibodies specific to EGFRvIII in 32 of 43 patients, with some patients developing titers>1:2,000,000. Production of high-affinity EGFRvIII-specific antibodies with an average of 6 nM (KD) was confirmed by analyzing EGFRvIII ECD using BIAcore SPR analysis.

It has often been challenging to clone MAbs directly from human B cells in an efficient way. In our preliminary results, the supernatant derived from human B-cells of a vaccinated GBM patient (ACT II-18) after stimulation with PEPvIII demonstrated positive reactivity on EGFRvIII transfected cells (NR6M) and wild-type EGFRwt transfectants (NR6W) at later days. With samples from our patients, we were able to transform B-cells with Epstein-Barr virus (EBV), and we demonstrated that these cells maintain their ability to secrete high-titer, EGFRvIII-specific antibodies after peptide stimulation for prolonged periods of at least 2 weeks. In our pilot studies, three out of four patient samples have been successfully transformed and demonstrated high-titer and high-affinity antibody production.

Example 2

To construct a recombinant bispecific T cell engaging molecule based on these human EGFRvIII-specific scFvs, we will subclone the human anti-EGFRvIII scFvs into an existing cassette, which we previously used to create an MR1-1×CD3 molecule, by substituting the MR1-1scFv portion. Mouse anti-human CD3 scFv was cloned from a hybridoma line OKT3 (ATCC, CRL 8001). MR1-1 bispecific T cell engaging protein after purification was shown in SDS-PAGE gel, with a molecular weight of 55 kDa. The MR1-1 bispecific T cell engaging molecule binds to EGFRvIII specifically and engages T-cells concomitantly through binding to CD3. EGFRvIII binding capacity and specificity was confirmed by using NR6M (EGFRvIII) and NR6W (EGFRwt) cell lines and a GBM cell line transfected with EGFRvIII (U87MG.ΔEGFR). Similarly, binding to CD3 was confirmed by staining human peripheral blood mononuclear cells (PBMCs) and Jurkat cells, showing the co-binding of either anti-CD4 or anti-CD8 with bispecific T cell engaging molecules on the same T-cell subpopulation from human PBMC or Jurkat cells. Although using human scFvs to generate bispecific T cell engaging molecules may reduce the generation of neutralizing antibodies and permit repeated administrations, the existing MR1-1 bispecific T cell engaging molecule may also be used.

Example 3

In order to minimize potential allogeneic responses against the tumor cells, we used our bank of existing matched human peripheral blood lymphocytes (PBLs) and GBM cell lines in these assays. Cytotoxicity of the MR1-1 bispecific T cell engaging molecule was measured by a standard chromium-release assay using unstimulated PBLs as effector cells and human GBM cell line U87MG, which expresses wild-type EGFR, and the transfected U87MG-EGFRvIII cell line as target cells. Results show that the MR1-1 construct is highly cytotoxic and antigen-specific, with a nearly 25-fold increase in specific lysis (%) for U87MGEGFRvIII over the wild-type control, U87MG. These results echo, if not exceed, the findings that were initially reported in vitro for bscCD19×CD34, a bispecific construct that has since been tested in human trials and found to induce potent tumor regression in patients with non-Hodgkin's lymphoma. The specific lysis by MR1-1 bispecific T cell engaging molecule was at 30% of U87 MG-EGFRvIII compared to ~1%-2% of control cells at 18 h, showing MR1-1 bispecific T cell engaging molecule mediated dose dependent specific lysis in vitro.

Example 4

The efficacy of MR1-1 bispecific T cell engaging molecule was evaluated in NSG mice. We have determined the MR1-1 bispecific T cell engaging molecule efficacy against U87MGEGFRvIII in NSG mice s.c. Briefly, U87 MG-EGFRIII cells (70%-80% confluence) were harvested with 0.25% Trypsin-EDTA. Cells were washed 2× with sterile PBS. PBLs were harvested as the non-adherent portion from healthy donor PBMC leukaphereses after a 1 h incubation in AIM-V 2% HABS. Three ×105 U87MG-EGFRvIII cells were mixed with 3×105 human PBLs (E:T of 1:1) and injected s.c. into the right flanks of 8 male NSG mice per group. Treatment by tail vein injections with 1 µg, 10 µg, 100 µg, and vehicle control was started 1 h after implantation of tumor cells. Treatment was repeated for four consecutive days. The results showed that the inhibition of subcutaneous U87MG-EGFRvIII tumor growth in NSG mice by MR1-1× CD3 was dose-dependent after 28 days of observation. Untreated tumor continued to grow steadily. There were two palpable tumors out of 8 in the 1-µg group. There was one palpable tumor in the 10-gig treated group. There were no tumors in the 100-µg treated group. The efficacy of MR1-1 bispecific T cell engaging molecule on the treatment of U87MG-EGFRvIII was very significant and encouraging in terms of the potency and dose dependency.

Example 5

EBV-transformed B cells provide only a transient reservoir of multi-clonal anti-EGFRvIII antibodies due to the high instability of viral incorporation into the human genome. To make stable lines that secrete antibody and to clone EGFRvIII-specific scFvs from these samples, we will use human hybridoma technology and electrofusion as previously described (13). Briefly, EBV-transformed PBMCs will be fused with hetermyeloma cell line HMMA2.5 by using a CytoPulse Hybrimune Electrofusion System (Cytopulse). Single cell clones will be screened by HAT (hypoxanthine, aminopterin, and thymidine) selection and confirmed by ELISA of supernatant against recombinant EGFRvIII ECD, or by flow cytometry against EGFRvIII expression cells lines and a cocktail of B-cell markers. Alternatively, we will construct a phage scFv display library expressing human immunoglobulin genes that can be screened on EGFRvIII ECD, and affinity-maturation will be done when needed, as previously described. Another approach will be to bypass the screening step by using high-throughput DNA sequencing and bioinformatic analysis to mine antibody variable region (V)-gene repertoires from plasma cells as described 19. VH and VL CDRs of the selected EGFRvIII-specific MAb-expressing hybridomas will be amplified by using isotype-specific primers, and scFv will be constructed in which the scFv protein has been tagged at the carboxy terminus with the hexahistidine sequences for purification and detection. Expression, production, and characterization of scFv will be carried out as described by using a metal affinity column. Binding of scFv will be confirmed by flow cytometry on cells expressing EGFRvIII. At least one fully human anti-EGFRvIII MAb will be isolated and its scFv is expected to have an affinity higher than MR1-1 (1.5 nM).

Example 6

To make the whole anti-EGFRvIII bispecific T cell engaging molecule human, we will generate a human scFv mimotope of murine MAb OKT3 that reacts with CD3 antigen via screening from a human scFv phage display library. The human scFv phagemid library (21), obtained from Los Alamos National Laboratory, has very high size (7.1×1013 pfu/mL) and diversity ($3\times10^{11}$). During selection, the biotinylated target antigen, CD3 (Sino Biological Inc.), is incubated with the scFv library, and complexes formed are captured upon magnetic streptavidin-coated beads. The bead+Ag/scFv complex is washed to remove nonspecific or low-affinity binding phage. The bead+Ag/scFv complex is treated with acid (0.1M HCl) to recover all scFvs that bind to the target antigen. To recover mimics of the mouse antibodies, the bead+Ag/scFv complex will be incubated with the corresponding mouse OKT3 IgG for competition/elution of the binding scFv antibodies. To generate those scFv antibodies with the highest affinity, the selection pressure will be increased through each round for 3 rounds. Once scFvs have been recovered that bind CD3, competition ELISA will be carried out to determine whether they are true mimics of the mouse OKT3, and affinity-maturation will be done if needed. We will then determine the T-cell activation function of 7 the human version OKT3 of anti-CD3 scFv by carrying out (a) T-lymphocyte proliferation assays, (b) cytokine release assays, and (c) detection of the expression of early T-cell activation marker by FACS as described (22).

Example 7

We will construct a human anti-EGFRvIII scFv and a human anti-CD3 scFv by linking VH and VL fragments with a (Gly4Ser)$_3$ peptide linker. A hexahistidine tag was introduced at the C-terminus of human anti-CD3 scFv to assist the detection and purification. Expression and purification of the new fully human anti-EGFRvIII bispecific T cell engaging molecule will follow the same protocol as described above for MR1-1 bispecific T cell engaging molecule according to our previous protocol.

Example 8

Building upon these promising preliminary data from our MR1-1 bispecific T cell engaging molecule studies, we will assess the cytotoxic activity of new fully human EGFRvIII-targeted bispecific T cell engaging molecules by following the same protocol as described above. Negative control experiments will be carried out with medium instead of bispecific T cell engaging molecule or effector cells. Specific lysis will then be calculated as [(cpm, experimental release)–(cpm, spontaneous release)]/[(cpm, maximal release)–(cpm, spontaneous release)].

Example 9

The efficacy of novel fully human EGFRvIII bispecific T cell engaging molecules will be evaluated in NSG mice as described previously, as well as in the preliminary studies. Our program has at its disposal a number of EGFRvIII-expressing human GBM xenografts and cell lines with matched autologous lymphocytes cryogenically preserved. Briefly, prior to bispecific T cell engaging molecule administration, tumor cells and lymphocytes will be mixed at a ratio of 1:1 and implanted in the caudate nucleus of the NSG mice using a Kopf stereotactic frame as we previously described(24). The NSG mouse model will provide "proof-of-concept" efficacy studies against a GBM expressing EGFRvIII in the CNS. Prior to beginning efficacy experiments, however, a maximum tolerated dose (MTD) of each candidate bispecific T cell engaging molecule will be established in these mice. Individual cohorts of 40 animals each will be administered a candidate molecule, with doses between groups increased by one half log 10 from 0.001 to 1 µg until an MTD is established. On the basis of prior work, mice will be treated intravenously (i.v.) with daily bispecific T cell engaging molecule doses for 5 days. Therapy at the MTD will start after approximately one-third of the median survival time has elapsed according to our prior experience with these tumors. Treatment will consist of the i.v. administration of the bispecific T cell engaging molecule construct at predetermined doses.

Example 10

Fully Human BiTE Design—We have generated cDNA encoding a fully human EGFRvIII-specific BiTE designated 139×28F11. The mAbs 139 (US 2010/0111979 A1) and 28F11 (U.S. Pat. No. 7,728,114 B2) are fully human antibodies with specificity for the EGFRvIII tumor antigen and the human CD3 complex, respectively. 28F11 has been described as the fully human analog for the murine OKT3 clone, and was selected in this approach for its ability to bind CD3 and induce T cell activation through this receptor similarly to OKT3.

We subcloned the VH and VL genes from a fully human anti-EGFRvIII mAb designated "139," and a fully human anti-CD3 activating mAb designated "28F11." Through well-known techniques, we have constructed human single-chain Fvs by linking the VH and VL fragments of each antibody with a (Gly4Ser)$_3$ peptide linker. We have previously performed these same manipulations for the commercially available human CD3-specific mAb OKT3 and the murine anti-EGFRvIII mAb MR1-1 to manufacture the existing MR1-1x OKT3 BiTE described above. Using this technique, we have generated a fully human BiTE—thus reducing the potential generation of neutralizing antibodies and permitting repeated administration—the existing MR1-1xOKT3 construct could be further investigated clinically as an alternative given previous success in clinical trials with BiTEs derived from murine antibodies.

Cytotoxicity of the 139×28F11 construct will be measured by standard chromium-release assay using unstimulated human peripheral blood lymphocytes (PBLs) as effector cells and human GBM cell lines U87MG and U87MG.ΔEGFR as target cells.

The xenograft system we used to obtain our preliminary data has the distinct advantage of evaluating drug candidates for efficacy in an animal system using human tumor tissue, with the potential to directly translate the therapeutic molecule of interest into clinical studies. However, a major drawback of this model is the lack of an endogenous immune system, which drastically impedes our ability to appropriately evaluate safety and toxicity of our molecule, as well as perform numerous mechanistic studies that may only be appropriately performed in syngeneic hosts. Importantly, other T cell activating antibodies have historically met with unforeseen toxicity when translated in early clinical trials, at least in part due to the lack of appropriate immunocompetent rodent models possessing surface molecules of equivalent binding affinities and function to those found in humans (25).

The use of human CD3 transgenic mice in the preclinical evaluation of our CD3-engaging BiTE, EGFRvIII×CD3, is unusual. These mice have been previously described to have ~3 copies of the human CD3 transgene integrated chromosomally at unknown locations (26). When heterozygous, tgε600± mice possess near-normal numbers of peripheral T cells that express both human and murine CD3. Notably, the tgε600± mouse strain has been successfully used to test the function of anti-human CD3 immunotoxins in preclinical models of T cell depletion and graft survival (27).

We have successfully imported the tgε600± mouse strain as embryos from Dr. Cox Terhorst (Beth Israel Deaconess Medical Center). We propose to establish a colony of tgε600±, and using our preexisting murine EGFRvIII-expressing cell lines as targets, we will first examine the ability for EGFRvIII×3 to redirect splenocytes from tgε600± mice against tumor cells in vitro by standard chromium release assay. After establishing minimum tumorigenic doses in the tgε600± mouse model, we will proceed with a validation of the results obtained from experiments we previously performed in the immunocompromised xenograft system.

Example 11

We codon optimized the nucleic acid encoding the human bispecific T cell engaging molecule for expression in CHO cells. Our human bispecific T cell engaging molecules included a signal sequence and a $V_L$-$V_H$ order for the EGFRvIII targeting portion of the molecule. It also contained linker molecules between each variable domain. We have found a molecule with this order to be more effective. We did not include a polyhistidine tag in the human bispecific T cell engaging molecule construct, which had been previously included to facilitate protein purification.

REFERENCES

The disclosure of each reference cited is expressly incorporated herein.

1. Stupp R, Mason WP, van den Bent MJ, et al: Radiotherapy plus Concomitant and Adjuvant Temozolomide for Glioblastoma. New England Journal of Medicine 352:987-996, 2005
2. Phan GQ, Yang JC, Sherry RM, et al: Cancer regression and autoimmunity induced by cytotoxic T lymphocyte-associated antigen 4 blockade in patients with metastatic melanoma. Proceedings of the National Academy of Sciences of the United States of America 100:8372-7, 2003
3. Suntharalingam G, Perry M R, Ward S, et al: Cytokine storm in a phase 1 trial of the anti-CD28 monoclonal antibody TGN1412. New England Journal of Medicine 355:1018-28, 2006
4. Bargou R, Leo E, Zugmaier G, et al: Tumor regression in cancer patients by very low doses of a T cell-engaging antibody. Science 321:974-7, 2008
5. Wikstrand C J, Hale L P, Batra S K, et al: Monoclonal antibodies against EGFRvIII are tumor specific and react with breast and lung carcinomas and malignant gliomas. Cancer Research 55:3140-8, 1995
6. Baeuerle P A, Reinhardt C: Bispecific T-cell engaging antibodies for cancer therapy. Cancer Research 69:4941-4, 2009
7. Bigner S H, Humphrey P A, Wong A J, et al: Characterization of the epidermal growth factor receptor in human glioma cell lines and xenografts. Cancer Research 50:8017-8022, 1990
8. Batra S K, Castelino-Prabhu S, Wikstrand C J, et al: Epidermal growth factor ligand-independent, unregulated, cell-transforming potential of a naturally occurring human mutant EGFRvIII gene. Cell Growth & Differentiation 6:1251-1259, 1995
9. Boockvar J A, Kapitonov D, Kapoor G, et al: Constitutive EGFR signaling confers a motile phenotype to neural stem cells. Molecular & Cellular Neurosciences 24:1116-30, 2003
10. Lammering G, Hewit T H, Holmes M, et al: Inhibition of the type III epidermal growth factor receptor variant mutant receptor by dominant-negative EGFR-CD533 enhances malignant glioma cell radiosensitivity. Clinical Cancer Research 10:6732-43, 2004
11. Montgomery R B, Guzman J, O'Rourke D M, et al: Expression of oncogenic epidermal growth factor receptor family kinases induces paclitaxel resistance and alters beta-tubulin isotype expression. Journal of Biological Chemistry 275:17358-63, 2000
12. Archer G E, Sampson J H, Lorimer I A, et al: Regional treatment of epidermal growth factor receptor vIII-expressing neoplastic meningitis with a single-chain immunotoxin, MR-1. Clinical Cancer Research 5:2646-52, 1999
13. Yu X, Tsibane T, McGraw PA, et al: Neutralizing antibodies derived from the B cells of 1918 influenza pandemic survivors. Nature 455:532-6, 2008.
14. Smith, K., arman, L., Wrammert, J., Zheng, N. Y., Capra, J. D., Ahmed, R., and Wilson, P. C. 2009. Rapid generation of fully human monoclonal antibodies specific to a vaccinating antigen. Nature Protocols 4(3): 372-384.
15. Heimberger A, Sun W, Hussain S, et al: Immunological responses in a patient with glioblastoma multiforme treated with sequential courses of temozolomide and immunotherapy. Neuro-Oncology 10:98-103, 2008
16. Wrammert J, Smith K, Miller J, et al: Rapid cloning of high-affinity human monoclonal antibodies against influenza virus. Nature 453:667-71, 2008
17. Wu X, Yang Z Y, Li Y, et al: Rational design of envelope identifies broadly neutralizing human monoclonal antibodies to HIV-1. Science 329:856-61, 2010
18. Beers, R., Chowdhury, P., Bigner, D. and Pastan, I.: Immunotoxins with increased activity against epidermal growth factor receptor vIII-expressing cells produced by antibody phage display. Clinical Cancer Research 6:2835-2843, 2000.
19. Reddy S T, Ge X, Miklos A E, et al: Monoclonal antibodies isolated without screening by analyzing the variable-gene repertoire of plasma cells. Nature Biotechnology 28:965-9, 2010
20. Kuan C T, Wikstrand C J, Archer G, et al: Increased binding affinity enhances targeting of glioma xenografts by EGFRvIII-specific scFv. International Journal of Cancer 88:962-9, 2000
21. Sblattero D, Bradbury A. Exploiting recombination in single bacteria to make large phage antibody libraries. Nature Biotechnology 18(1):75-80, 2000.
22. Li B, Wang H, Dai J, et al: Construction and characterization of a humanized anti-human CD3 monoclonal antibody 12F6 with effective immunoregulation functions. Immunology 116:487-98, 2005
23. Kuan C T, Reist C J, Foulon C F, et al: 125I-labeled anti-epidermal growth factor receptor-vIII single-chain Fv exhibits specific and high-level targeting of glioma xenografts. Clinical Cancer Research 5:1539-49, 1999
24. Heimberger A B, Learn C A, Archer G E, et al: Brain tumors in mice are susceptible to blockade of epidermal growth factor receptor (EGFR) with the oral, specific, EGFR-tyrosine kinase inhibitor ZD1839 (iressa). Clinical Cancer Research 8:3496-502, 2002
25. Attarwala H (2010) TGN1412: From Discovery to Disaster. (Translated from eng) Journal of young pharmacists: JYP 2(3):332-336 (in eng).
26. Wang, Wang, Salio, Allen, She, and Terhorst.: Expression of a CD3epsiolon transgene in CD3epsilon$^{null}$ mice does not restore CD3 gamma and delta expression but efficiently rescues T cell development from a subpopulation of prothymocytes. International Immunology 12:1777-1788, 1998
27. Weetall M, Digan ME, Hugo R, et al.: T-cell depletion and graft survival induced by anti-human CD3 immunotoxins in human CD3epsilon transgenic mice. Transplantation. 73:1658-66, 2002.

We claim:

1. A bispecific polypeptide, comprising:
a first single chain human variable region which binds to EGFRvIII, and comprises segments as set forth in SEQ ID NO: 5 and 6 in amino to carboxy order; in series with
a second single chain human variable region which binds to T cell activation ligand CD3 and comprises segments as set forth in SEQ ID NO: 7 and 8 in amino to carboxy order; wherein the first and second single chain human variable regions are in amino to carboxy order, wherein a linker sequence intervenes between each of said segments, wherein the linker sequence is $(G_4S)_3$; SEQ ID NO: 9), wherein a spacer polypeptide links the first and second single chain variable regions, and wherein the spacer polypeptide is ($G_4S$; SEQ ID NO: 10).

2. The bispecific polypeptide of claim 1 which comprises segments as set forth in SEQ ID NO: 4, 5, 9, 6, 10, 7, 9, and 8, in amino to carboxy order.

3. The bispecific polypeptide of claim 1 wherein each single chain variable region comprises a disulfide bond between the VH and the VL domain.

4. A polynucleotide encoding the bispecific polypeptide of claim 1.

5. The polynucleotide of claim 4 comprising the sequence of SEQ ID NO: 1.

6. A method of making a bispecific polypeptide comprising:
culturing a cell comprising the polynucleotide of claim 4 in a culture medium, wherein the bispecific polyeptide is expressed, and collecting the bispecific polypeptide from the cells or culture medium.

7. A method of making a bispecific polypeptide comprising:
culturing a cell comprising the polynucleotide of claim 5 in a culture medium, wherein the bispecific polyeptide is expressed, and collecting the bispecific polypeptide from the cells or culture medium.

8. A method of treating a patient with an EGFRvIII-expressing tumor, comprising: administering the bispecific polypeptide of claim 1 to the patient, whereby a cytolytic T cell response to the tumor is induced.

* * * * *

SEQUENCE LISTING

<160> NUMBER OF SEQ ID NOS: 10

<210> SEQ ID NO 1
<211> LENGTH: 1506
<212> TYPE: DNA
<213> ORGANISM: Artificial Sequence
<220> FEATURE:
<223> OTHER INFORMATION: modified human sequence construct; codon optimized for expression in CHO cells

```
<400> SEQUENCE: 1
atgaagtggg tgacctttat tagcctgctg ttcctgttct cctccgccta ttccgacatc      60
cagatgactc agagcccttc ttccctgtca gcttccgtgg gcgacagggt caccatcaca     120
tgccgggctt cccagggaat tagaaacaat ctggcatggt accagcagaa gccaggcaaa     180
gcccccaagc gcctgatcta tgccgcttct aacctgcaga gtggagtgcc ctcacgattc     240
acaggcagcg gatctgggac agagtttact ctgattgtct ccagcctgca gccagaagat     300
ttcgccactt actattgcct gcagcaccat tcctaccccc tgacaagcgg cggagggact     360
aaagtggaga tcaagggtgg aggaggatct ggtggaggag aagtggtgg aggaggatca      420 gaggtgcagg tcctggaaag cggtggagga ctggtgcagc aggaggttc cctgcgtctg      480 agctgtgcag cctctggctt cacctttct agttatgcaa tgtcctgggt cgcgccaggca     540 cctggcaagg gactggaatg ggtcagcgca atcagtggct caggcggaag tacaaactac     600
gccgactcag tgaaaggaag gttcaccatt agtcgcgata actcaaagaa tactctgtat     660
ctgcagatga atagcctgcg ggccgaggac accgctgtgt actattgcgc tggctcatcc     720
ggatggtctg aatactgggg acaggggacc ctggtgacag tcagctctgg gggtggcgga     780
tctcaggtgc agctggtcga gagtggaggt ggagtggtcc agccaggaag gtccctgcga     840
ctgagctgtg ctgcatctgg tttcaaattt tctggttacg gcatgcactg ggtgagacag     900
gctcccggaa aggggctgga atgggtgcca gtcatctggt atgacggaag caagaaatac     960
tatgtggatt ctgtcaaagg gcgattcacc attagtcgtg ataactcaaa gaatacactg    1020
tacctgcaaa tgaatagctt acgggcagag gacactgccg tgtactattg cgctagacag    1080
atgggctatt ggcattttga tctgtggggt cgcggcactc tggtgaccgt cagttctgga    1140
ggaggtggat ccggaggagg tggaagcgga ggggtggct ctgagatcgt gctgacccag     1200
tctccagcaa cactgtccct gagccctgga gaacgcgcca cactgtcctg tcgagcttct    1260
cagagtgtgt ccagctacct ggcctggtat cagcagaagc tggccaggc tccacgactg     1320 ctgatctacg acgcttccaa ccgtgcaact ggcattcctg ctaggttctc aggatccggg    1380
agcggtaccg actttactct gaccatctct agtctggagc agaagatttt cgcagtgtac    1440
tattgtcagc agaggagcaa ttggcccccct ctgacttttg gagggggtac caaagtcgag    1500
attaag                                                              1506

<210> SEQ ID NO 2
<211> LENGTH: 502
<212> TYPE: PRT
<213> ORGANISM: Artificial Sequence
<220> FEATURE:
<223> OTHER INFORMATION: modified human sequence construct; complete
      amino acid sequence including  signal peptide

<400> SEQUENCE: 2

Met Lys Trp Val Thr Phe Ile Ser Leu Leu Phe Leu Phe Ser Ser Ala
 1               5                  10                  15

Tyr Ser Asp Ile Gln Met Thr Gln Ser Pro Ser Ser Leu Ser Ala Ser
                20                  25                  30

Val Gly Asp Arg Val Thr Ile Thr Cys Arg Ala Ser Gln Gly Ile Arg
            35                  40                  45

Asn Asn Leu Ala Trp Tyr Gln Gln Lys Pro Gly Lys Ala Pro Lys Arg
        50                  55                  60

Leu Ile Tyr Ala Ala Ser Asn Leu Gln Ser Gly Val Pro Ser Arg Phe
65                  70                  75                  80
```

-continued

```
Thr Gly Ser Gly Ser Gly Thr Glu Phe Thr Leu Ile Val Ser Ser Leu
                85                  90                  95
Gln Pro Glu Asp Phe Ala Thr Tyr Tyr Cys Leu Gln His His Ser Tyr
            100                 105                 110
Pro Leu Thr Ser Gly Gly Thr Lys Val Glu Ile Lys Gly Gly Gly Gly
        115                 120                 125
Gly Ser Gly Gly Gly Gly Ser Gly Gly Gly Ser Glu Val Gln Val
    130                 135                 140
Leu Glu Ser Gly Gly Gly Leu Val Gln Pro Gly Gly Ser Leu Arg Leu
145                 150                 155                 160
Ser Cys Ala Ala Ser Gly Phe Thr Phe Ser Ser Tyr Ala Met Ser Trp
                165                 170                 175
Val Arg Gln Ala Pro Gly Lys Gly Leu Glu Trp Val Ser Ala Ile Ser
            180                 185                 190
Gly Ser Gly Gly Ser Thr Asn Tyr Ala Asp Ser Val Lys Gly Arg Phe
        195                 200                 205
Thr Ile Ser Arg Asp Asn Ser Lys Asn Thr Leu Tyr Leu Gln Met Asn
    210                 215                 220
Ser Leu Arg Ala Glu Asp Thr Ala Val Tyr Tyr Cys Ala Gly Ser Ser
225                 230                 235                 240
Gly Trp Ser Glu Tyr Trp Gly Gln Gly Thr Leu Val Thr Val Ser Ser
                245                 250                 255
Gly Gly Gly Gly Ser Gln Val Gln Leu Val Glu Ser Gly Gly Gly Val
            260                 265                 270
Val Gln Pro Gly Arg Ser Leu Arg Leu Ser Cys Ala Ala Ser Gly Phe
        275                 280                 285
Lys Phe Ser Gly Tyr Gly Met His Trp Val Arg Gln Ala Pro Gly Lys
    290                 295                 300
Gly Leu Glu Trp Val Ala Val Ile Trp Tyr Asp Gly Ser Lys Lys Tyr
305                 310                 315                 320
Tyr Val Asp Ser Val Lys Gly Arg Phe Thr Ile Ser Arg Asp Asn Ser
                325                 330                 335
Lys Asn Thr Leu Tyr Leu Gln Met Asn Ser Leu Arg Ala Glu Asp Thr
            340                 345                 350
Ala Val Tyr Tyr Cys Ala Arg Gln Met Gly Tyr Trp His Phe Asp Leu
        355                 360                 365
Trp Gly Arg Gly Thr Leu Val Thr Val Ser Ser Gly Gly Gly Gly Ser
    370                 375                 380
Gly Gly Gly Gly Ser Gly Gly Gly Ser Glu Ile Val Leu Thr Gln
385                 390                 395                 400
Ser Pro Ala Thr Leu Ser Leu Ser Pro Gly Glu Arg Ala Thr Leu Ser
                405                 410                 415
Cys Arg Ala Ser Gln Ser Val Ser Ser Tyr Leu Ala Trp Tyr Gln Gln
            420                 425                 430
Lys Pro Gly Gln Ala Pro Arg Leu Leu Ile Tyr Asp Ala Ser Asn Arg
        435                 440                 445
Ala Thr Gly Ile Pro Ala Arg Phe Ser Gly Ser Gly Ser Gly Thr Asp
    450                 455                 460
Phe Thr Leu Thr Ile Ser Ser Leu Glu Pro Glu Asp Phe Ala Val Tyr
465                 470                 475                 480
```

Tyr Cys Gln Gln Arg Ser Asn Trp Pro Pro Leu Thr Phe Gly Gly Gly
                485                 490                 495

Thr Lys Val Glu Ile Lys
            500

<210> SEQ ID NO 3
<211> LENGTH: 484
<212> TYPE: PRT
<213> ORGANISM: Artificial Sequence
<220> FEATURE:
<223> OTHER INFORMATION: modified human sequence construct; mature amino
      acid seuqence

<400> SEQUENCE: 3

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asn
             20                  25                  30

Leu Ala Trp Tyr Gln Gln Lys Pro Gly Lys Ala Pro Lys Arg Leu Ile
         35                  40                  45

Tyr Ala Ala Ser Asn Leu Gln Ser Gly Val Pro Ser Arg Phe Thr Gly
 50                  55                  60

Ser Gly Ser Gly Thr Glu Phe Thr Leu Ile Val Ser Ser Leu Gln Pro
65                  70                  75                  80

Glu Asp Phe Ala Thr Tyr Tyr Cys Leu Gln His His Ser Tyr Pro Leu
                85                  90                  95

Thr Ser Gly Gly Gly Thr Lys Val Glu Ile Lys Gly Gly Gly Gly Ser
            100                 105                 110

Gly Gly Gly Gly Ser Gly Gly Gly Gly Ser Glu Val Gln Val Leu Glu
        115                 120                 125

Ser Gly Gly Gly Leu Val Gln Pro Gly Gly Ser Leu Arg Leu Ser Cys
130                 135                 140

Ala Ala Ser Gly Phe Thr Phe Ser Ser Tyr Ala Met Ser Trp Val Arg
145                 150                 155                 160

Gln Ala Pro Gly Lys Gly Leu Glu Trp Val Ser Ala Ile Ser Gly Ser
                165                 170                 175

Gly Gly Ser Thr Asn Tyr Ala Asp Ser Val Lys Gly Arg Phe Thr Ile
            180                 185                 190

Ser Arg Asp Asn Ser Lys Asn Thr Leu Tyr Leu Gln Met Asn Ser Leu
        195                 200                 205

Arg Ala Glu Asp Thr Ala Val Tyr Tyr Cys Ala Gly Ser Ser Gly Trp
210                 215                 220

Ser Glu Tyr Trp Gly Gln Gly Thr Leu Val Thr Val Ser Ser Gly Gly
225                 230                 235                 240

Gly Gly Ser Gln Val Gln Leu Val Glu Ser Gly Gly Gly Val Val Gln
                245                 250                 255

Pro Gly Arg Ser Leu Arg Leu Ser Cys Ala Ala Ser Gly Phe Lys Phe
            260                 265                 270

Ser Gly Tyr Gly Met His Trp Val Arg Gln Ala Pro Gly Lys Gly Leu
        275                 280                 285

Glu Trp Val Ala Val Ile Trp Tyr Asp Gly Ser Lys Lys Tyr Tyr Val
290                 295                 300

Asp Ser Val Lys Gly Arg Phe Thr Ile Ser Arg Asp Asn Ser Lys Asn
305                 310                 315                 320

```
Thr Leu Tyr Leu Gln Met Asn Ser Leu Arg Ala Glu Asp Thr Ala Val
                325                 330                 335

Tyr Tyr Cys Ala Arg Gln Met Gly Tyr Trp His Phe Asp Leu Trp Gly
        340                 345                 350

Arg Gly Thr Leu Val Thr Val Ser Ser Gly Gly Gly Ser Gly Gly
    355                 360                 365

Gly Gly Ser Gly Gly Gly Ser Glu Ile Val Leu Thr Gln Ser Pro
370                 375                 380

Ala Thr Leu Ser Leu Ser Pro Gly Glu Arg Ala Thr Leu Ser Cys Arg
385                 390                 395                 400

Ala Ser Gln Ser Val Ser Ser Tyr Leu Ala Trp Tyr Gln Gln Lys Pro
                405                 410                 415

Gly Gln Ala Pro Arg Leu Leu Ile Tyr Asp Ala Ser Asn Arg Ala Thr
                420                 425                 430

Gly Ile Pro Ala Arg Phe Ser Gly Ser Gly Ser Gly Thr Asp Phe Thr
                435                 440                 445

Leu Thr Ile Ser Ser Leu Glu Pro Glu Asp Phe Ala Val Tyr Tyr Cys
            450                 455                 460

Gln Gln Arg Ser Asn Trp Pro Pro Leu Thr Phe Gly Gly Gly Thr Lys
465                 470                 475                 480

Val Glu Ile Lys

<210> SEQ ID NO 4
<211> LENGTH: 18
<212> TYPE: PRT
<213> ORGANISM: Artificial Sequence
<220> FEATURE:
<223> OTHER INFORMATION: signal peptide

<400> SEQUENCE: 4

Met Lys Trp Val Thr Phe Ile Ser Leu Leu Phe Leu Phe Ser Ser Ala
  1               5                  10                  15

Tyr Ser

<210> SEQ ID NO 5
<211> LENGTH: 107
<212> TYPE: PRT
<213> ORGANISM: Artificial Sequence
<220> FEATURE:
<223> OTHER INFORMATION: modified human sequence construct; anti-
      EGFRvIII VL sequence

<400> SEQUENCE: 5

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asn
                20                  25                  30

Leu Ala Trp Tyr Gln Gln Lys Pro Gly Lys Ala Pro Lys Arg Leu Ile
            35                  40                  45

Tyr Ala Ala Ser Asn Leu Gln Ser Gly Val Pro Ser Arg Phe Thr Gly
        50                  55                  60

Ser Gly Ser Gly Thr Glu Phe Thr Leu Ile Val Ser Ser Leu Gln Pro
65                  70                  75                  80

Glu Asp Phe Ala Thr Tyr Tyr Cys Leu Gln His His Ser Tyr Pro Leu
                85                  90                  95

Thr Ser Gly Gly Gly Thr Lys Val Glu Ile Lys
                100                 105
```

```
<210> SEQ ID NO 6
<211> LENGTH: 116
<212> TYPE: PRT
<213> ORGANISM: Artificial Sequence
<220> FEATURE:
<223> OTHER INFORMATION: modified human sequence construct; anti-
      EGFRvIII VH sequence

<400> SEQUENCE: 6

Glu Val Gln Val Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Asn Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Gly Ser Ser Gly Trp Ser Glu Tyr Trp Gly Gln Gly Thr Leu Val
            100                 105                 110

Thr Val Ser Ser
        115

<210> SEQ ID NO 7
<211> LENGTH: 118
<212> TYPE: PRT
<213> ORGANISM: Artificial Sequence
<220> FEATURE:
<223> OTHER INFORMATION: modified human sequence construct; anti-CD3VH
      sequence

<400> SEQUENCE: 7

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Lys Phe Ser Gly Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Lys Lys Tyr Tyr Val Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gln Met Gly Tyr Trp His Phe Asp Leu Trp Gly Arg Gly Thr
            100                 105                 110

Leu Val Thr Val Ser Ser
        115

<210> SEQ ID NO 8
<211> LENGTH: 108
<212> TYPE: PRT
<213> ORGANISM: Artificial Sequence
<220> FEATURE:
<223> OTHER INFORMATION: modified human sequence construct; anti-CD3 VL
      sequence
```

```
<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Leu Thr Phe Gly Gly Gly Thr Lys Val Glu Ile Lys
                100                 105

<210> SEQ ID NO 9
<211> LENGTH: 15
<212> TYPE: PRT
<213> ORGANISM: Artificial Sequence
<220> FEATURE:
<223> OTHER INFORMATION: linker 1

<400> SEQUENCE: 9

Gly Gly Gly Gly Ser Gly Gly Gly Gly Ser Gly Gly Gly Gly Ser
1               5                   10                  15

<210> SEQ ID NO 10
<211> LENGTH: 5
<212> TYPE: PRT
<213> ORGANISM: Artificial Sequence
<220> FEATURE:
<223> OTHER INFORMATION: linker 2

<400> SEQUENCE: 10

Gly Gly Gly Gly Ser
1               5
```